US012636482B2

(12) United States Patent
Kuriyama et al.

(10) Patent No.: US 12,636,482 B2
(45) Date of Patent: May 26, 2026

(54) CONNECTOR SET AND FEMALE CONNECTOR

(71) Applicant: TERUMO KABUSHIKI KAISHA, Tokyo (JP)

(72) Inventors: Tasuku Kuriyama, Kai (JP); Toshihiko Kakinoki, Oyama (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 859 days.

(21) Appl. No.: 17/942,789

(22) Filed: Sep. 12, 2022

(65) Prior Publication Data

US 2023/0001173 A1 Jan. 5, 2023

Related U.S. Application Data

(63) Continuation of application No. PCT/JP2021/001264, filed on Jan. 15, 2021.

(30) Foreign Application Priority Data

Mar. 19, 2020 (JP) ................................. 2020-050040

(51) Int. Cl.
| | |
|---|---|
| *A61M 39/10* | (2006.01) |
| *A61M 39/20* | (2006.01) |
| *A61M 39/26* | (2006.01) |

(52) U.S. Cl.
CPC ........ *A61M 39/10* (2013.01); *A61M 39/1011* (2013.01); *A61M 39/20* (2013.01);
(Continued)

(58) Field of Classification Search
CPC .............. A61M 39/10; A61M 39/1011; A61M 39/20; A61M 39/26; A61M 2039/1083;
(Continued)

(56) References Cited

U.S. PATENT DOCUMENTS

| | | | | |
|---|---|---|---|---|
| 2018/0214683 A1* | 8/2018 | Ueda | ...................... | A61M 39/04 |
| 2019/0240473 A1* | 8/2019 | Tsunoda | ................ | A61M 39/26 |

FOREIGN PATENT DOCUMENTS

| | | |
|---|---|---|
| JP | 2013-252165 A | 12/2013 |
| JP | 2014-030489 A | 2/2014 |

(Continued)

OTHER PUBLICATIONS

International Searching Authority, "Written Opinion," issued in connection with International Patent Application No. PCT/JP2021/001264, dated Mar. 9, 2021 with English translation.

(Continued)

*Primary Examiner* — Bhisma Mehta
*Assistant Examiner* — Marissa Taylor
(74) *Attorney, Agent, or Firm* — Foley & Lardner LLP

(57) ABSTRACT

A connector set includes a male connector; and a female connector. The male connector includes: a hollow rod-shaped flow path connection portion that defines a first flow path therein and that has a first axis as a center, and a lock protrusion that has an inner peripheral edge extending in a circumferential direction around the first axis. The female connector includes: a cap, a housing, and a valve body. The cap includes: a top wall, and a cylindrical outer peripheral wall extending from an outer peripheral edge of the top wall and that has a second axis as a center. The housing includes: a cylindrical wall, and an engagement protrusion protruding from an outer peripheral surface of the cylindrical wall so as to form a lower surface configured to engage with the lock protrusion to lock the male connector.

10 Claims, 7 Drawing Sheets

(52) U.S. Cl.
CPC ..... *A61M 39/26* (2013.01); *A61M 2039/1083*
(2013.01); *A61M 2039/1088* (2013.01)

(58) Field of Classification Search
CPC ............. A61M 2039/1088; A61M 2039/1016;
A61M 2039/1044; A61M 2039/1072
See application file for complete search history.

(56)                     References Cited

FOREIGN PATENT DOCUMENTS

| JP | 2015073664 A | * | 4/2015 | |
| JP | 2019-201777 A | | 11/2019 | |
| WO | WO-2014021390 A1 | * | 2/2014 | ............ A61M 5/162 |

OTHER PUBLICATIONS

International Searching Authority, "International Search Report,"
issued in connection with International Patent Application No.
PCT/JP2021/001264, dated Mar. 9, 2021.
International Searching Authority, "Written Opinion," issued in
connection with International Patent Application No. PCT/JP2021/
001264, dated Mar. 9, 2021.

* cited by examiner

CONNECTOR SET AND FEMALE CONNECTOR

CROSS-REFERENCE TO RELATED APPLICATIONS

This is a bypass continuation of PCT Application No. PCT/JP2021/001264, filed on Jan. 15, 2021, which claims priority to Japanese Application No. JP2020-050040, filed on Mar. 19, 2020. The contents of these applications are hereby incorporated by reference in their entireties.

BACKGROUND

The present disclosure relates to a connector set and a female connector.

A medical tube or the like is used to form a liquid delivery line and a liquid such as a medicinal solution or blood is delivered through the liquid delivery line to perform infusion, blood transfusion, artificial dialysis, and the like. Medical devices such as a medical tube and a syringe used in the liquid delivery line can be connected to each other by using a connector set including a male connector and a female connector to which the male connector can be connected (see, for example, JP 2013-252165 A).

The male connector includes a hollow rod-shaped flow path connection portion that defines a first flow path inside, and a lock protrusion. The female connector includes a cap, a housing, and a valve body. The cap has a top wall having an opening into which the flow path connection portion provided in the male connector can be inserted, and an outer peripheral wall hanging from an outer peripheral edge of the top wall. The housing has a cylindrical wall having an inner peripheral surface defining a second flow path, and an engagement protrusion protruding from an outer peripheral surface of the cylindrical wall so as to form a lower surface to be engaged with the lock protrusion to lock the male connector in a state of being connected to the female connector. The valve body includes a clamped portion that is clamped by the top wall and the cylindrical wall, and a through hole portion that is located in the opening in a top view and that penetrates the valve body in an up-down direction.

SUMMARY

Regarding the connector set in the related art as described above, due to a dimensional accuracy, an assembly accuracy, and the like of each member, a gap may be formed at a boundary formed between an upper surface of the engagement protrusion of the housing and a lower end surface of the outer peripheral wall of the cap. Then, in cases such as one where a locked state where the lock protrusion is engaged with the lower surface of the engagement protrusion is released by an unintended external force, an inner peripheral edge of the lock protrusion may be engaged with the above gap, and although the connector set is not in a normal connected state, the connector set may be continued to be used as it is because it is difficult to determine from the appearance.

Therefore, an object of the present disclosure is to provide a female connector and a connector set capable of inhibiting an inner peripheral edge of a lock protrusion of a male connector from being engaged with a boundary between an engagement protrusion and an outer peripheral wall of the female connector.

According to a first aspect of the disclosure, a connector set includes: a male connector; and a female connector configured to connect the male connector. The male connector includes a hollow rod-shaped flow path connection portion that defines a first flow path inside and has a first axis as a center, and a lock protrusion that has an inner peripheral edge extending along a circumferential direction of the first axis. The female connector includes a cap, a housing, and a valve body. The cap has a top wall having an opening configured to be inserted by the flow path connection portion, and a cylindrical outer peripheral wall that extends from an outer peripheral edge of the top wall and that has a second axis as a center. The housing has a cylindrical wall having an inner peripheral surface defining a second flow path, and an engagement protrusion protruding from an outer peripheral surface of the cylindrical wall so as to form a lower surface to be engaged with the lock protrusion to lock the male connector in a state of being connected to the female connector. The valve body includes a clamped portion that is clamped by the top wall and the cylindrical wall, and a through hole portion that is located in the opening in a top view and that penetrates the valve body in an up-down direction. A boundary is formed between an upper surface of the engagement protrusion and a lower end surface of the outer peripheral wall. The boundary does not include a portion that has a length equal to or longer than a length of the inner peripheral edge of the lock protrusion and that extends along a circumferential direction of the second axis.

According to an embodiment of the present disclosure, a portion that extends along the circumferential direction of the second axis and a portion that does not extend along the circumferential direction of the second axis are alternately connected in the circumferential direction of the second axis to form the boundary.

According to an embodiment of the present disclosure, the boundary includes only the portion that does not extend along the circumferential direction of the second axis.

According to an embodiment of the present disclosure, the portion that does not extend along the circumferential direction of the second axis has a polygonal or curved waveform.

According to an embodiment of the present disclosure, the portion that does not extend along the circumferential direction of the second axis has a linear shape or a curved shape inclined in the up-down direction toward the circumferential direction of the second axis.

According to an embodiment of the present disclosure, an outer peripheral surface of the engagement protrusion and an outer peripheral surface of the outer peripheral wall are flush with each other at the boundary.

According to a second aspect of the disclosure, a female connector is configured to connect to a male connector that includes a hollow rod-shaped flow path connection portion that defines a first flow path inside and that has a first axis as a center, and a lock protrusion that has an inner peripheral edge extending along a circumferential direction of the first axis. The female connector includes a cap, a housing, and a valve body. The cap has a top wall having an opening configured to be inserted by the flow path connection portion, and a cylindrical outer peripheral wall that extends from an outer peripheral edge of the top wall and that has a second axis as a center. The housing includes a cylindrical wall having an inner peripheral surface defining a second flow path, and an engagement protrusion protruding from an outer peripheral surface of the cylindrical wall so as to form a lower surface to be engaged with the lock protrusion to lock the male connector in a state of being connected to the female connector. The valve body includes a clamped portion that is clamped by the top wall and the cylindrical wall, and a through hole portion that is located in the opening in a top view and that penetrates the valve body in an up-down direction. A boundary is formed between an upper surface of the engagement protrusion and a lower end surface of the outer peripheral wall. The boundary includes only a portion that does not extend along a circumferential direction of the second axis.

According to certain embodiments of the present disclosure, a female connector and a connector set can be provided that are capable of inhibiting an inner peripheral edge of a lock protrusion of a male connector from being engaged with a boundary between an engagement protrusion and an outer peripheral wall of the female connector.

DETAILED DESCRIPTION

Figure 1:
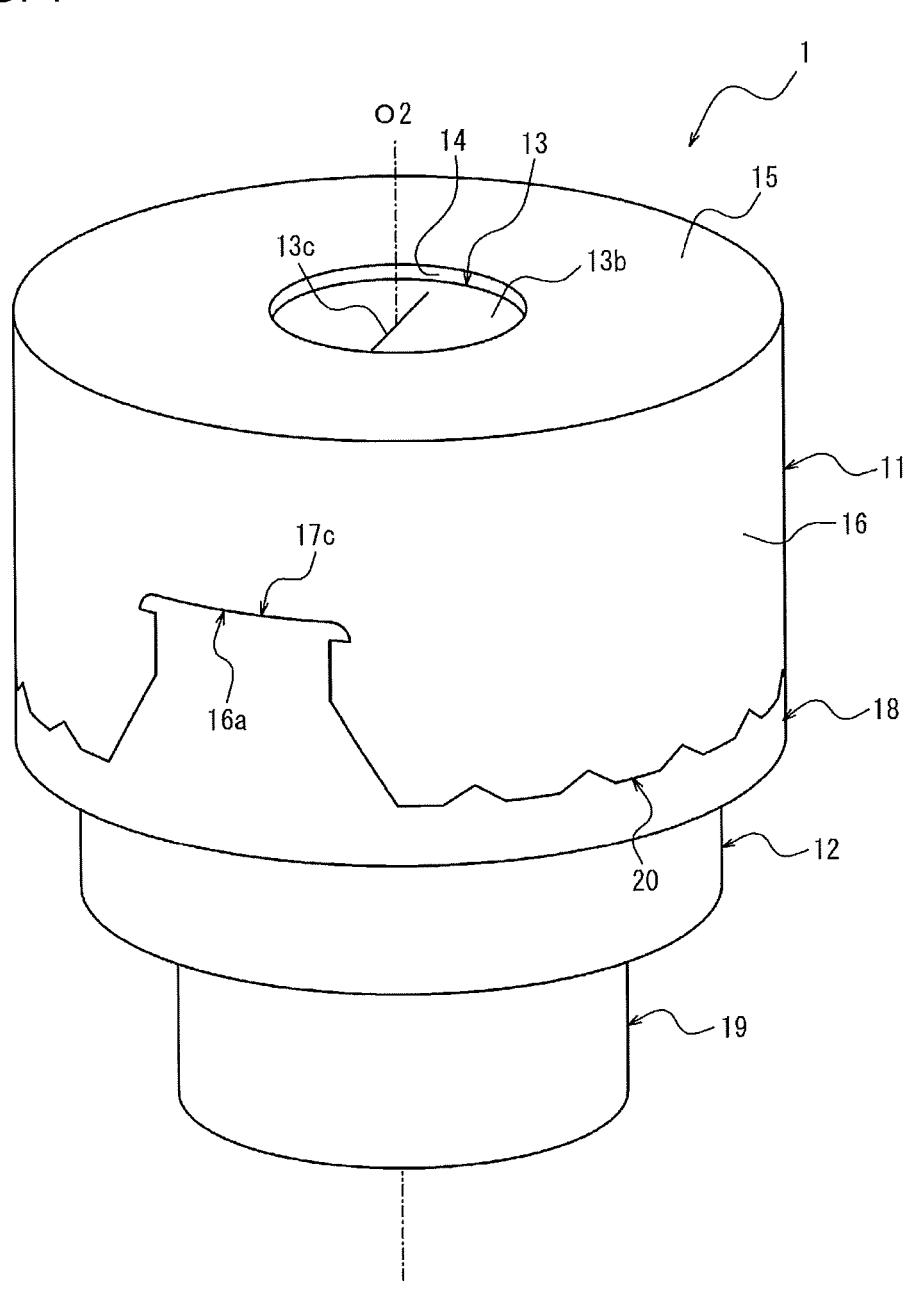
FIG. 1 is a perspective view illustrating a female connector as a first embodiment.

Hereinafter, embodiments according to the present disclosure will be described in detail with reference to FIGS. 1 to 9. In the drawings, corresponding elements are denoted by the same reference signs.

In each embodiment, regarding a female connector 1, a direction along a second axis O2 that is a central axis of an outer peripheral wall 16 of a cap 11 is referred to as an up-down direction, a direction directed from a top wall 15 of the cap 11 toward a housing 12 along the second axis O2 (a lower direction in FIG. 5) is referred to as a lower direction, an opposite direction of the lower direction is referred to as an upper direction, a direction around the second axis O2 is referred to as a circumferential direction, and a direction orthogonal to the second axis O2 is referred to as a radial direction. In addition, in each embodiment, regarding a male connector 2, a direction along a first axis O1 that is a central axis of a flow path connection portion 4 is referred to as an up-down direction, a direction directed from a proximal end (base end) to a distal end of the flow path connection portion 4 along the first axis O1 (the lower direction in FIG. 5) is referred to as a lower direction, an opposite direction of the lower direction is referred to as an upper direction, a direction around the first axis O1 is referred to as a circumferential direction, and a direction orthogonal to the first axis O1 is referred to as a radial direction. A term regarding the up-down direction does not define orientations of the female connector 1 and the male connector 2 at the time of use. For example, the female connector 1 and the male connector 2 may be used such that the second axis O2 or the first axis O1 is perpendicular to a vertical direction.

Figure 2:
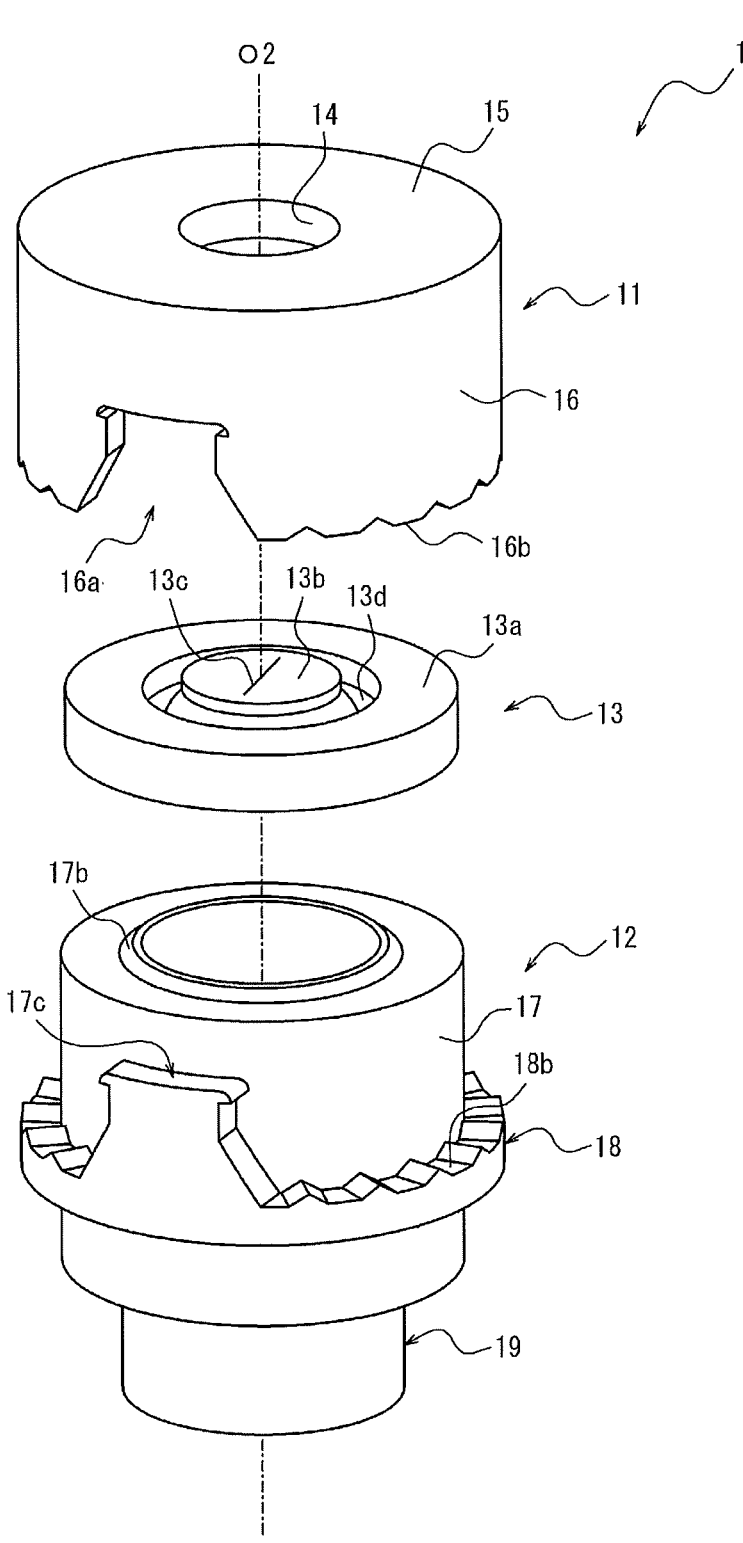
FIG. 2 is an exploded perspective view of the female connector illustrated in FIG. 1.
Figure 3:
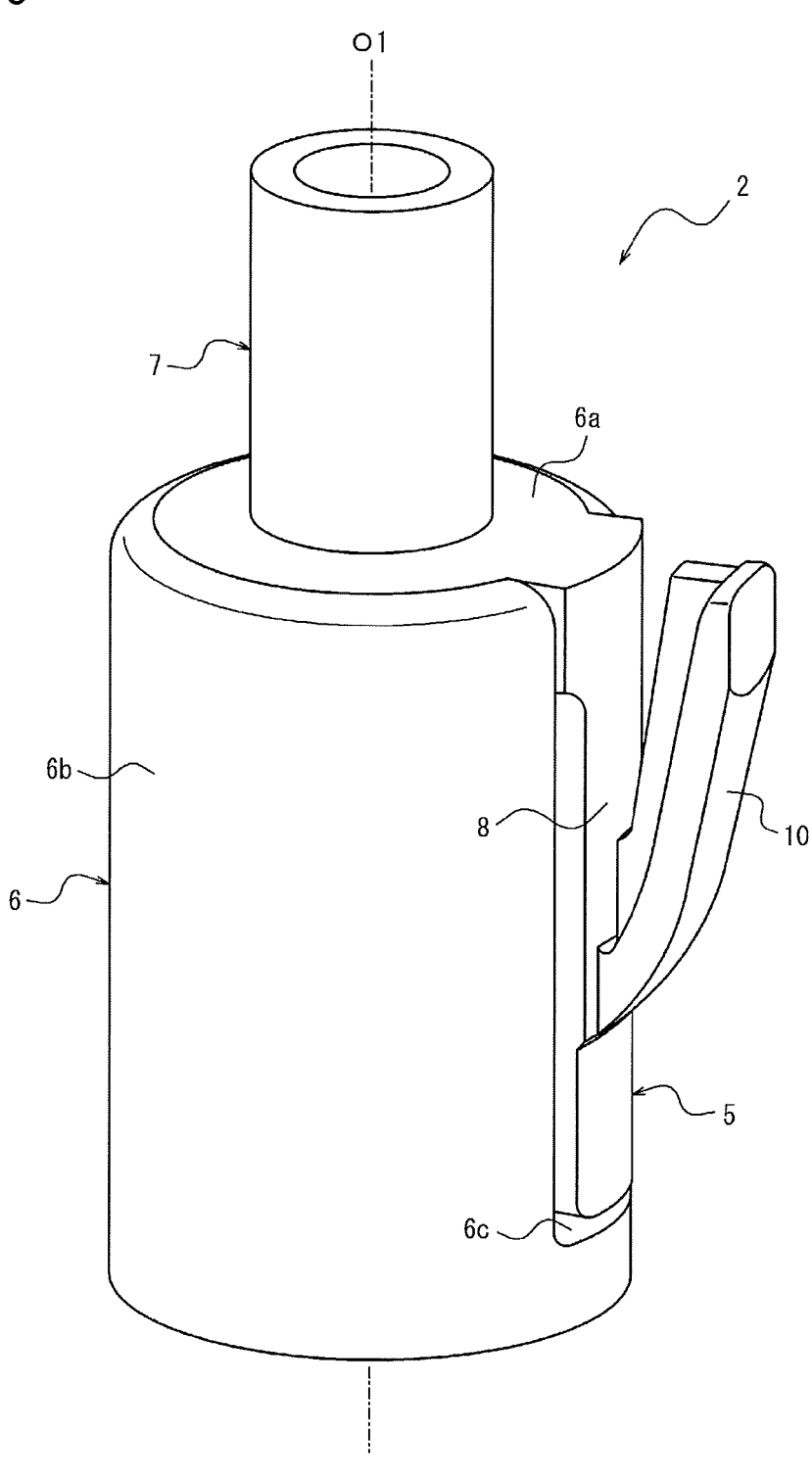
FIG. 3 is a perspective view illustrating a male connector configured to be connected to the female connector illustrated in FIG. 1.
Figure 4:
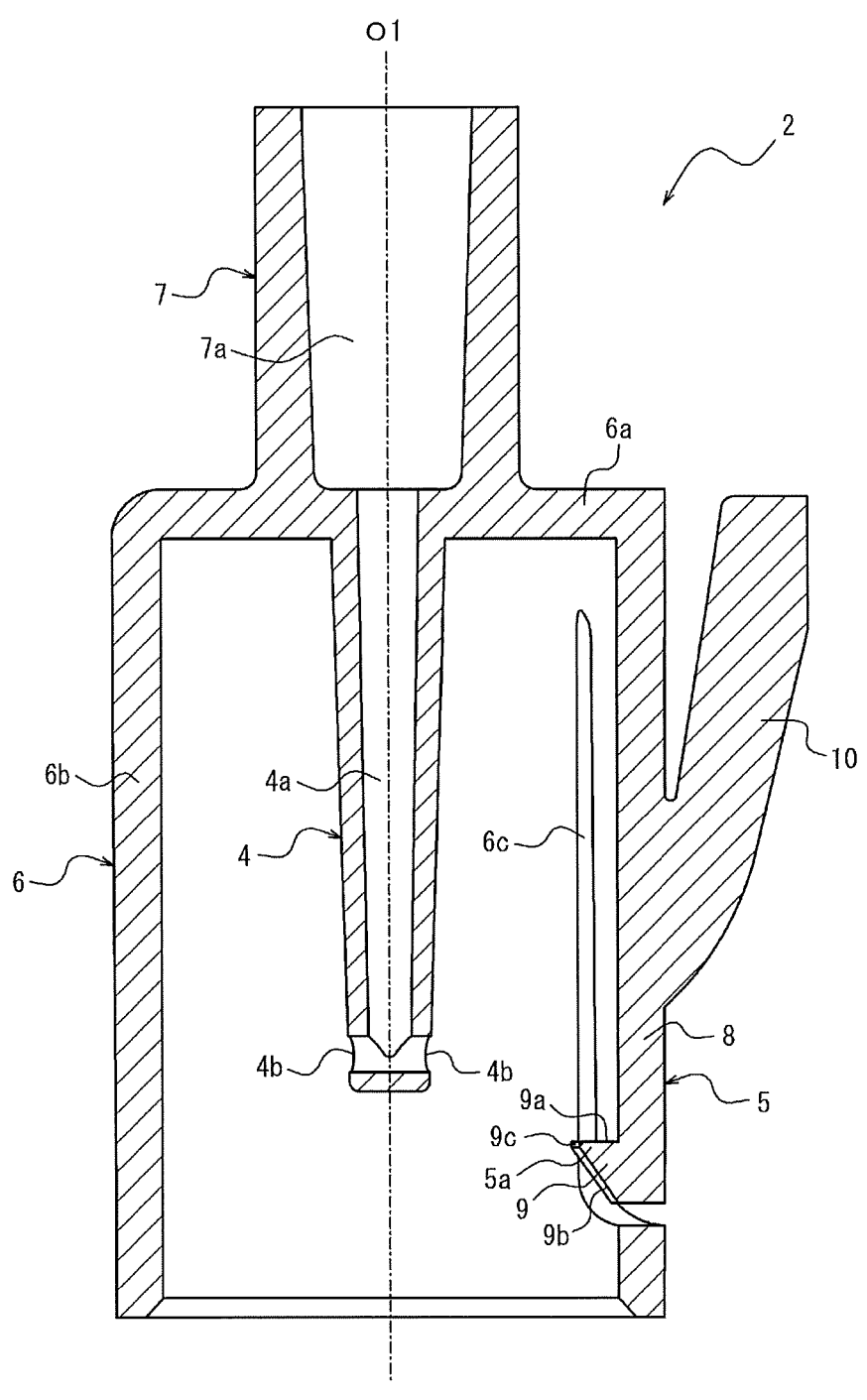
FIG. 4 is a cross-sectional view of the male connector illustrated in FIG. 3.
Figure 5:
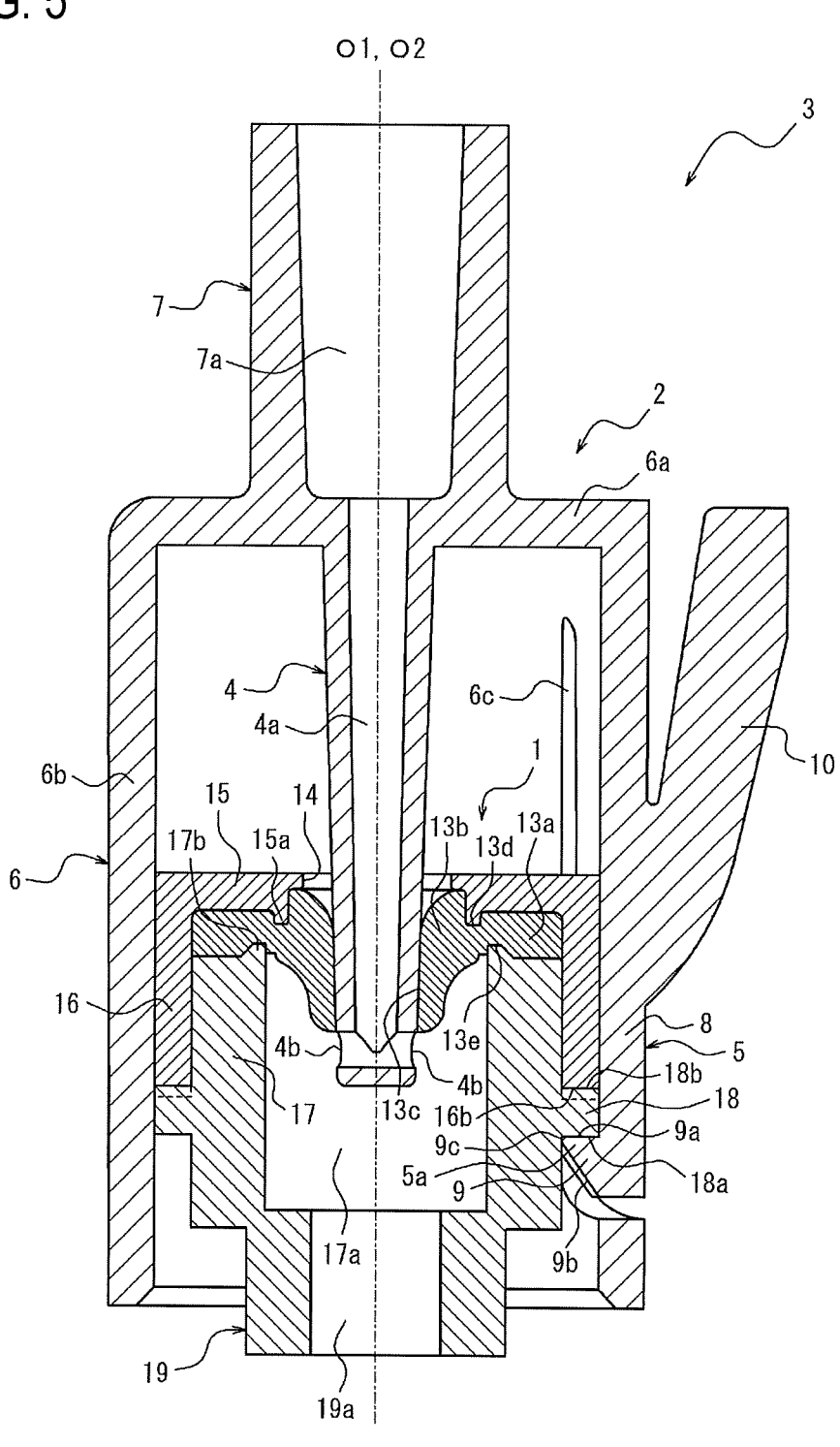
FIG. 5 is a cross-sectional view illustrating a locked state when the male connector illustrated in FIG. 3 is connected to the female connector illustrated in FIG. 1.

The female connector 1 according to a first embodiment illustrated in FIGS. 1, 2, 5, and 6 can be connected to the male connector 2 illustrated in FIGS. 3 to 5. The female connector 1 and the male connector 2 constitute a connector set 3. The connector set 3 is used to connect medical devices such as a medical tube and a syringe used in a liquid delivery line (not illustrated) through which a liquid such as a medicinal solution or blood is delivered from the outside of the body to the inside of the body or from the inside of the body to the outside of the body for infusion, blood transfusion, artificial dialysis, or the like. The liquid delivery line in which the connector set 3 is used is, for example, an infusion line through which a liquid is delivered from the outside of the body to the inside of the body.

As illustrated in FIGS. 3 to 5, the male connector 2 includes the flow path connection portion 4, a lock claw 5, a cover 6, and a first tube connection portion 7. The male connector 2 is an integrally molded product made of a synthetic resin.

The flow path connection portion 4 has a hollow rod shape that defines a first flow path 4a inside. More specifically, the flow path connection portion 4 has a bottomed cylindrical shape with a diameter gradually decreasing in the lower direction and having the first axis O1 as a center, and has two through holes 4b penetrating in the radial direction at a distal portion.

The lock claw 5 includes a cantilevered arm 8 extending in the lower direction from a fixed end, and a lock protrusion 9 protruding toward an inner side in the radial direction from a lower end (free end) of the arm 8.

Figure 7:
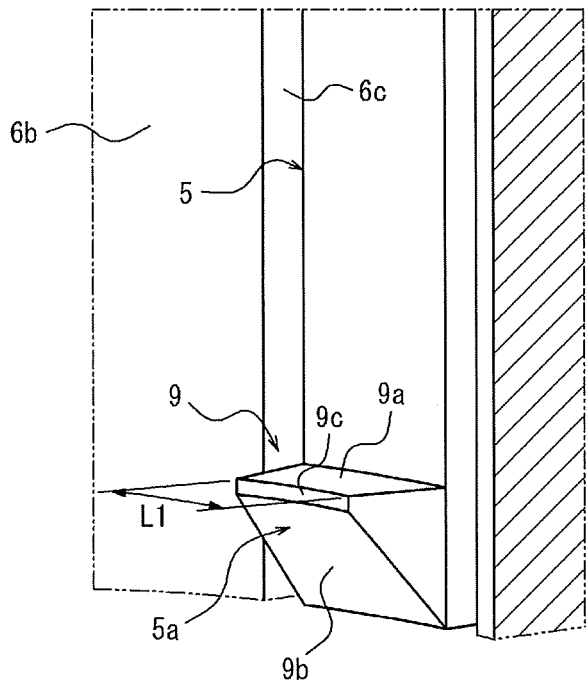
FIG. 7 is a perspective view illustrating a lock claw of the male connector illustrated in FIG. 3.
Figure 8:
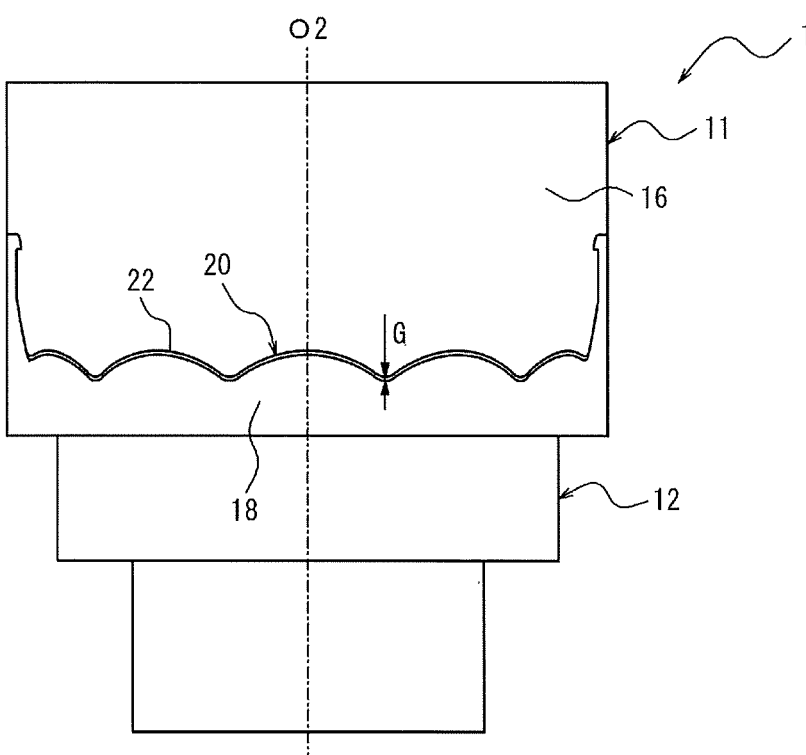
FIG. 8 is a side view illustrating a female connector as a second embodiment.

As illustrated in FIG. 7, the lock protrusion 9 has a horizontal upper surface 9a and a tapered lower surface 9b that is gradually inclined in the lower direction toward an outer side in the radial direction. A tapered lock claw tip 5a is formed on an inner peripheral edge of the upper surface 9a and an inner peripheral edge of the lower surface 9b. An inner peripheral edge of the lock claw tip 5a, that is, an inner peripheral edge 9c of the lock protrusion 9, extends along the circumferential direction of the first axis O1.

An operation lever 10 is connected to an outer peripheral surface of the arm 8. The operation lever 10 extends in a direction inclined in the upper direction toward the outer side in the radial direction, from an intermediate portion in the up-down direction on the outer peripheral surface of the arm 8.

The cover 6 has a horizontal top wall 6a and a cylindrical outer wall 6b that extends from an outer peripheral edge of the top wall 6a and that has the first axis O1 as a center. The proximal end of the flow path connection portion 4 is continuous with the top wall 6a. The outer wall 6b is connected to an upper end of the arm 8 of the lock claw 5. The outer wall 6b has a notch 6c, and the arm 8 is located in the notch 6c.

The first tube connection portion 7 has a cylindrical shape having the first axis O1 as a center. An upper surface of the top wall 6a is connected to a lower end of the first tube connection portion 7. An inner peripheral surface of the first tube connection portion 7 defines a first tube connection portion flow path 7a communicating with the first flow path 4a of the flow path connection portion 4. A medical tube is to be connected to the first tube connection portion 7.

As illustrated in FIGS. 1, 2, 5, and 6, the female connector 1 includes the cap 11, the housing 12, and a valve body 13.

The cap 11 and the housing 12 are integrally molded products made of a synthetic resin, respectively. The valve body 13 is an integrally molded product made of an elastic material such as rubber or an elastomer.

The cap 11 has the top wall 15 having an opening 14 configured to be inserted by the flow path connection portion 4 provided in the male connector 2, and the outer peripheral wall 16 hanging from an outer peripheral edge of the top wall 15. The opening 14 has a circular shape in a top view. The top wall 15 has an annular shape in the top view. A lower surface of the top wall 15 has a first support protrusion 15*a* that extends continuously or intermittently in the circumferential direction and that protrudes in the lower direction. The outer peripheral wall 16 has notch-shaped fitted portions 16*a* that are provided at two positions facing each other with the second axis O2 interposed therebetween and that open toward the lower direction. The outer peripheral wall 16 has a cylindrical shape having the second axis O2 as a center.

The housing 12 has a cylindrical wall 17, an engagement protrusion 18, and a second tube connection portion 19.

The cylindrical wall 17 has an inner peripheral surface that defines a second flow path 17*a*. An upper surface of the cylindrical wall 17 has a second support protrusion 17*b* that extends continuously or intermittently in the circumferential direction and that protrudes in the upper direction. An outer peripheral surface of the cylindrical wall 17 has fitting portions 17*c* that are respectively fitted to the two fitted portions 16*a* of the cap 11 in order to fix the cap 11 to the housing 12. The fitting portions 17*c* are disposed at two positions facing each other with the second axis O2 interposed therebetween, on an upper direction side of the engagement protrusion 18. Each of the fitting portions 17*c* (and the fitted portions 16*a*) has a T-shape in a side view. The outer peripheral surface of the cylindrical wall 17 has a cylindrical shape.

The engagement protrusion 18 protrudes from the outer peripheral surface of the cylindrical wall 17 so as to form a lower surface 18*a* that engages with the upper surface 9*a* of the lock protrusion 9 of the lock claw 5 to lock the male connector 2 in a state of being connected to the female connector 1 (that is, a connected state).

Figure 6:
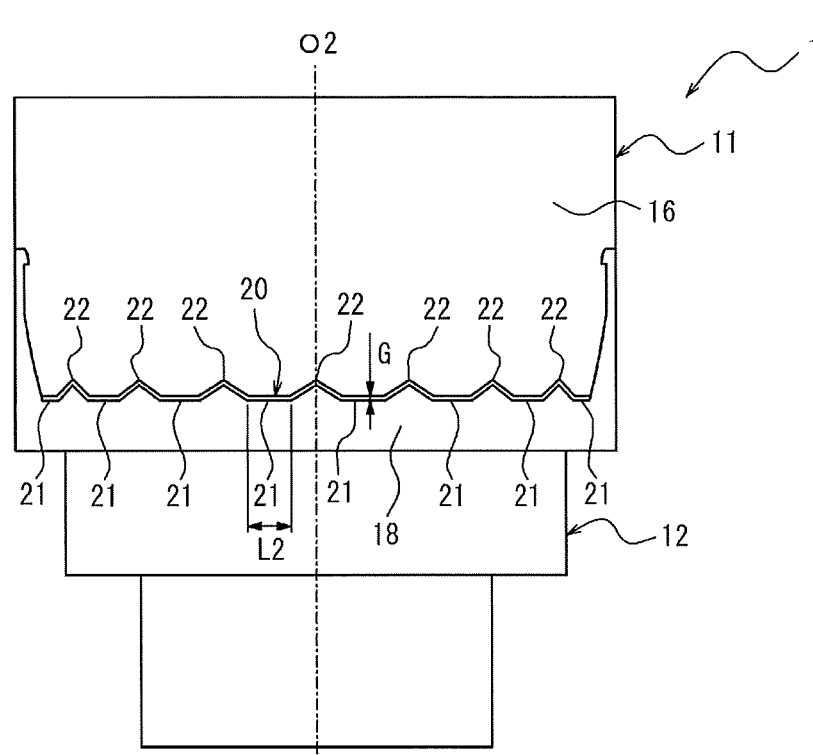
FIG. 6 is a side view of the female connector illustrated in FIG. 1.

As illustrated in FIG. 6, a boundary 20 is formed between an upper surface 18*b* of the engagement protrusion 18 and a lower end surface 16*b* of the outer peripheral wall 16 of the cap 11. A gap G may be formed at the boundary 20 due to a dimensional accuracy, an assembly accuracy, and the like of each member.

An outer peripheral surface of the engagement protrusion 18 and an outer peripheral surface of the outer peripheral wall 16 are flush with each other at the boundary 20. In addition, the outer peripheral surface of the engagement protrusion 18 has a fixed outer diameter over the circumferential direction. The outer diameter of the engagement protrusion 18 is equal to an inner diameter of the cover 6.

The boundary 20 does not include a portion that extends along the circumferential direction of the second axis O2 and that has a length equal to or longer than a first length L1 that is a length (that is, a length in the circumferential direction) of the inner peripheral edge 9*c* of the lock protrusion 9. More specifically, portions 21 (hereinafter, also referred to as the first portions 21) that extend along the circumferential direction of the second axis O2 and portions 22 (hereinafter, also referred to as the second portions 22) that do not extend along the circumferential direction of the second axis O2 are alternately connected in the circumferential direction of the second axis O2 to form the boundary 20. A second length L2, which is a length of each of the first portions 21, is smaller than the first length L1. Each of the second portions 22 has a polygonal waveform (more specifically, a single polygonal waveform). Note that each of the second portions 22 may have a plurality of polygonal waveforms or a curved waveform (a single waveform or a plurality of waveforms) instead of the single polygonal waveform.

As illustrated in FIGS. 1, 5, and the like, the second tube connection portion 19 has a cylindrical shape having the second axis O2 as a center. A lower end of the cylindrical wall 17 is connected to an upper end of the second tube connection portion 19. An inner peripheral surface of the second tube connection portion 19 defines a second tube connection portion flow path 19*a* communicating with the second flow path 17*a* of the cylindrical wall 17. A medical tube is connected to the second tube connection portion 19.

As illustrated in FIGS. 1, 2, and 5, the valve body 13 includes a clamped portion 13*a*, a partition wall portion 13*b*, and a through hole portion 13*c*. The clamped portion 13*a* is clamped by the top wall 15 and the cylindrical wall 17. The partition wall portion 13*b* has the through hole portion 13*c* implemented by a slit having a straight line shape in the top view. The through hole portion 13*c* is located in the opening 14 in the top view and penetrates the valve body 13 in the up-down direction. The partition wall portion 13*b* has a disk shape having the second axis O2 as a center. The clamped portion 13*a* has an annular shape connected to an outer peripheral edge of the partition wall portion 13*b*.

An upper surface of the valve body 13 has an upper annular groove 13*d* extending along an inner peripheral edge of the clamped portion 13*a*. The first support protrusion 15*a* of the cap 11 is configured to bite into the upper annular groove 13*d*. A lower surface of the valve body 13 has a lower annular groove 13*e* extending along the inner peripheral edge of the clamped portion 13*a*. The second support protrusion 17*b* of the housing 12 is configured to bite into the lower annular groove 13*e*.

The partition wall portion 13*b* closes one end of the second flow path 17*a* of the cylindrical wall 17 in a state where the male connector 2 is not connected to the female connector 1 (that is, non-connected state). In addition, the through hole portion 13*c* of the partition wall portion 13*b* is passed through by the flow path connection portion 4 of the male connector 2 to allow the first flow path 4*a* to communicate with the second flow path 17*a*, as illustrated in FIG. 5, in a state (that is, a locked state) where the lock protrusion 9 and the engagement protrusion 18 are locked by engagement thereof in the connected state. In the locked state, the second axis O2, which is the central axis of the outer peripheral wall 16 of the cap 11, substantially coincides with the first axis O1, which is the central axis of the flow path connection portion 4.

When connecting the male connector 2 to the female connector 1, because the outer peripheral surface of the engagement protrusion 18 and the outer peripheral surface of the outer peripheral wall 16 are flush with each other at the boundary 20, the male connector 2 can be smoothly connected to enter the locked state (see FIG. 5). In addition, when connecting the male connector 2 to the female connector 1, the female connector 1 can be guided by an inner peripheral surface of the outer wall 6*b* of the cover 6. In the locked state, the locked state can be favorably maintained by contact between the inner peripheral surface of the outer wall 6*b* of the cover 6 and the outer peripheral surface of the engagement protrusion 18.

In addition, in the present embodiment, because the outer peripheral surface of the engagement protrusion 18 has the fixed outer diameter over the circumferential direction, the lock protrusion 9 can be engaged with the engagement protrusion 18 at any position in the circumferential direction. Therefore, it is unnecessary to provide a structure for regulating a rotation position of the female connector 1 in the circumferential direction with respect to the male connector 2, whereby a simple structure and a simple connection operation can be implemented.

In order to release the locked state, a tip of the arm 8 of the lock claw 5 is displaced toward the outer side in the radial direction by operating the operation lever 10, and the male connector 2 may be moved relatively in the upper direction with respect to the female connector 1 in a state where the engagement between the lock protrusion 9 and the engagement protrusion 18 is released.

In addition, although not illustrated, in a case where the boundary 20 includes only the first portion 21 that extends along the circumferential direction of the second axis O2, the inner peripheral edge 9c of the lock protrusion 9 may be engaged with the gap G formed at the boundary 20, for example, when the locked state is released by an unintended external force, and this state may be maintained even though the connected state is abnormal. In particular, when the flow path connection portion 4 has the through holes 4b penetrating in the radial direction at the distal portion as in the present embodiment, the through holes 4b may be closed by the partition wall portion 13b of the valve body 13.

However, it is difficult to determine such an abnormal connected state from the appearance. Then, if the connector set is continued to be used in the abnormal connected state, intended delivering of a liquid is not performed, and a serious situation may occur.

In this regard, in the present embodiment, as described above, the boundary 20 does not include the portion that extends along the circumferential direction of the second axis O2 and that has the length equal to or longer than the first length L1 that is the length of the inner peripheral edge 9c of the lock protrusion 9. Therefore, the inner peripheral edge 9c of the lock protrusion 9 can be inhibited from being engaged with the boundary 20 (more specifically, the lower end surface 16b of the outer peripheral wall 16).

In the first embodiment, the first portions 21 that extend along the circumferential direction of the second axis O2 and the second portions 22 that do not extend along the circumferential direction of the second axis O2 in the circumferential direction of the second axis O2 are alternately connected to form the boundary 20. Alternatively, as in a second embodiment illustrated in FIG. 8, the boundary 20 may include only the second portion 22 that does not extend along the circumferential direction of the second axis O2. More specifically, the second portion 22 has a curved waveform. According to such a configuration, because the boundary 20 does not include the portion that has the length equal to or longer than the first length L1 and that extends along the circumferential direction of the second axis O2, an occurrence that the inner peripheral edge 9c of the lock protrusion 9 is engaged with the boundary 20 to cause an abnormal connected state similar to the above can be inhibited. Note that the second portion 22 may have a polygonal waveform instead of the curved waveform.

Figure 9:
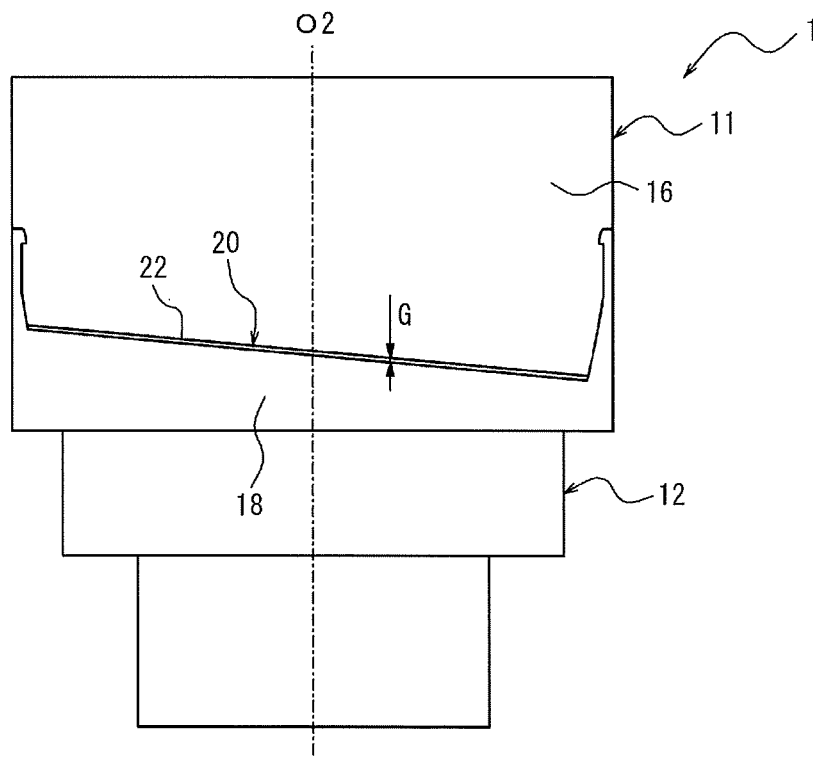
FIG. 9 is a side view illustrating a female connector as a third embodiment.

In addition, as in a third embodiment illustrated in FIG. 9, the boundary 20 may include only the second portion 22 that does not extend along the circumferential direction of the second axis O2, and the second portion 22 may have a linear shape inclined in the up-down direction toward the circumferential direction of the second axis O2. According to such a configuration, because the boundary 20 does not include the portion that has the length equal to or longer than the first length L1 and that extends along the circumferential direction of the second axis O2, an occurrence that the inner peripheral edge 9c of the lock protrusion 9 is engaged with the boundary 20 to cause an abnormal connected state similar to the above can be inhibited. Note that the second portion 22 may have a curved shape inclined in the up-down direction toward the circumferential direction of the second axis O2, instead of the linear shape inclined in the up-down direction toward the circumferential direction of the second axis O2.

The above-described embodiments are merely examples of the present disclosure, and for example, various modifications as described below can be made.

The male connector 2 may include the hollow rod-shaped flow path connection portion 4 that defines the first flow path 4a inside and that has the first axis O1 as a center, and the lock protrusion 9 that has the inner peripheral edge 9c extending along the circumferential direction of the first axis O1. The number and arrangement of the through holes 4b formed in the flow path connection portion 4 can be appropriately changed. The through hole 4b may be provided so as to penetrate the flow path connection portion 4 in the up-down direction. The structure of the portion connected to the proximal end of the flow path connection portion 4 to form the flow path communicating with the first flow path 4a is not limited to the first tube connection portion 7, and various modifications can be made. A shape and arrangement of the operation lever 10 can be appropriately changed. The lock claw 5 is not limited to one operated by the operation lever 10. The lock claw 5 is not limited to one including the cantilevered arm 8. The male connector 2 is not limited to one including the cover 6.

The male connector 2 may be configured as a closed connector having an elastic valve body that closes the flow path connection portion 4 in the non-connected state and exposes the distal end of the flow path connection portion 4 in the connected state. The male connector 2 may have two or more lock claws 5.

The cap 11 may have the top wall 15 having the opening 14 configured to be inserted by the flow path connection portion 4, and the cylindrical outer peripheral wall 16 that extends from the outer peripheral edge of the top wall 15 and that has the second axis O2 as a center. The opening 14 is not limited to the circular shape in the top view.

The housing 12 may include the cylindrical wall 17 having the inner peripheral surface defining the second flow path 17a, and the engagement protrusion 18 protruding from the outer peripheral surface of the cylindrical wall 17 so as to form the lower surface 18a to be engaged with the lock protrusion 9 to lock the male connector 2 in the state of being connected to the female connector 1. The structure of the portion connected to the lower end of the cylindrical wall 17 to form the flow path communicating with the second flow path 17a is not limited to the second tube connection portion 19, and various modifications can be made.

The valve body 13 includes the clamped portion 13a that is clamped by the top wall 15 and the cylindrical wall 17, and the through hole portion 13c that is positioned in the opening 14 in the top view and penetrates the valve body 13 in the up-down direction. The clamped portion 13a is not limited to the annular shape in the top view. The through hole portion 13c is not limited to be implemented by a slit having a straight line shape in the top view, and may be, for example, an X-shaped or Y-shaped slit in the top view or a portion other than the slit.

The female connector 1 may have the cap 11, the housing 12, and the valve body 13, the boundary 20 may be formed between the upper surface 18b of the engagement protrusion 18 and the lower end surface 16b of the outer peripheral wall 16, and the boundary 20 may not include the portion that extends along the circumferential direction of the second axis O2 and that has the length equal to or longer than the first length L1 that is the length of the inner peripheral edge 9c of the lock protrusion 9. The outer peripheral surface of the engagement protrusion 18 is not limited to one having a fixed outer diameter over the circumferential direction. The female connector 1 is not limited to one in which the cap 11 and the housing 12 are fixed by the fitted portions 16a and the fitting portions 17c.

What is claimed is:

1. A connector set comprising:
a male connector; and
a female connector configured to connect the male connector; wherein:
the male connector comprises:
    a hollow rod-shaped flow path connection portion that defines a first flow path therein and that has a first axis as a center, and
    a lock protrusion that has an inner peripheral edge extending in a circumferential direction around the first axis,
the female connector comprises:
    a cap,
    a housing, and
    a valve body, wherein:
the cap comprises:
    a top wall comprising an opening configured to receive the flow path connection portion, and
    a cylindrical outer peripheral wall extending from an outer peripheral edge of the top wall and that has a second axis as a center,
the housing comprises:
    a cylindrical wall having an inner peripheral surface defining a second flow path, and
    an engagement protrusion protruding from an outer peripheral surface of the cylindrical wall so as to form a lower surface configured to engage with the lock protrusion to lock the male connector in a state of being connected to the female connector,
the valve body comprises:
    a clamped portion that is clamped by the top wall and the cylindrical wall, and
    a through hole portion that is located in the opening in a top view and that penetrates the valve body in an up-down direction,
    a boundary is formed between an upper surface of the engagement protrusion and a lower end surface of the outer peripheral wall, and
    the boundary does not include a portion that satisfies both conditions (i) having a length equal to or longer than a length of the inner peripheral edge of the lock protrusion, and (ii) extending in a circumferential direction around the second axis.

2. The connector set according to claim 1, wherein:
the boundary is formed of a plurality of first portions that extend in the circumferential direction around the second axis and a plurality of second portions that do not extend in the circumferential direction of the second axis, the first and second portions being alternately connected in the circumferential direction of the second axis.

3. The connector set according to claim 2, wherein:
in a side view, the second portion that does not extend along the circumferential direction of the second axis has a shape of a polygonal or curved waveform.

4. The connector set according to claim 2, wherein:
in a side view, the second portion that does not extend along the circumferential direction of the second axis has a linear shape that is inclined in the up-down direction toward the circumferential direction of the second axis or a curved shape that is inclined in the up-down direction toward the circumferential direction of the second axis.

5. The connector set according to claim 1, wherein:
no portion of the boundary extends along the circumferential direction of the second axis.

6. The connector set according to claim 3, wherein
in a side view, an entirety of the boundary has a shape of a polygonal or curved waveform.

7. The connector set according to claim 3, wherein:
in a side view, an entirety of the boundary has a linear shape or a curved shape that is inclined in the up-down direction toward the circumferential direction of the second axis.

8. The connector set according to claim 1, wherein:
an outer peripheral surface of the engagement protrusion and an outer peripheral surface of the outer peripheral wall are flush with each other at the boundary.

9. A female connector configured to connect to a male connector comprising a hollow rod-shaped flow path connection portion that defines a first flow path therein and that has a first axis as a center, and a lock protrusion that has an inner peripheral edge extending in a circumferential direction around the first axis, the female connector comprising:
a cap,
a housing, and
a valve body, wherein:
the cap comprises:
    a top wall comprising an opening configured to receive the flow path connection portion, and
    a cylindrical outer peripheral wall extending from an outer peripheral edge of the top wall and that has a second axis as a center;
the housing comprises:
    a cylindrical wall having an inner peripheral surface defining a second flow path, and
    an engagement protrusion protruding from an outer peripheral surface of the cylindrical wall so as to form a lower surface configured to engage with the lock protrusion to lock the male connector in a state of being connected to the female connector;
the valve body comprises:
    a clamped portion that is clamped by the top wall and the cylindrical wall, and
    a through hole portion that is located in the opening in a top view and that penetrates the valve body in an up-down direction;
a boundary is formed between an upper surface of the engagement protrusion and a lower end surface of the outer peripheral wall; and
the boundary does not include a portion that satisfies both conditions (i) having a length equal to or longer than a length of the inner peripheral edge of the lock protrusion, and (ii) extending in a circumferential direction around the second axis.

10. A connector set comprising:

a male connector; and a female connector configured to connect the male connector; wherein:

the male connector comprises:

a hollow rod-shaped flow path connection portion that defines a first flow path therein and that has a first axis as a center, and a lock protrusion that has an inner peripheral edge extending in a circumferential direction around the first axis, the female connector comprises:

a cap, a housing, and a valve body, wherein:

the cap comprises:

a top wall comprising an opening configured to receive the flow path connection portion, and a cylindrical outer peripheral wall extending from an outer peripheral edge of the top wall and that has a second axis as a center, the housing comprises:

a cylindrical wall having an inner peripheral surface defining a second flow path, and an engagement protrusion protruding from an outer peripheral surface of the cylindrical wall so as to form a lower surface configured to engage with the lock protrusion to lock the male connector in a state of being connected to the female connector, the valve body comprises:

a clamped portion that is clamped by the top wall and the cylindrical wall, and a through hole portion that is located in the opening in a top view and that penetrates the valve body in an up-down direction, a boundary is formed between an upper surface of the engagement protrusion and a lower end surface of the outer peripheral wall, and the boundary is formed of a plurality of first portions that extend in the circumferential direction around the second axis and a plurality of second portions that do not extend in the circumferential direction of the second axis, the first and second portions being alternately connected in the circumferential direction of the second axis, and a length of each of the first portions is less than a length of the inner peripheral edge of the lock protrusion.

* * * * *